United States Patent
Luo (10) Patent No.: US 11,843,905 B2
(45) Date of Patent: *Dec. 12, 2023

(54) SENSOR DEVICE, SENSING METHOD, AND PROGRAM STORAGE MEDIUM

(71) Applicant: NEC Corporation, Tokyo (JP)

(72) Inventor: Yuan Luo, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/862,655

(22) Filed: Jul. 12, 2022

(65) Prior Publication Data

US 2022/0345799 A1    Oct. 27, 2022

Related U.S. Application Data (63) Continuation of application No. 16/650,023, filed as application No. PCT/JP2017/034840 on Sep. 27, 2017, now Pat. No. 11,418,860.

(51) Int. Cl.
*H04Q 9/00* (2006.01)
*H04Q 9/02* (2006.01)

(52) U.S. Cl.
CPC ........... *H04Q 9/02* (2013.01); *H04Q 2209/40* (2013.01); *H04Q 2209/826* (2013.01)

(58) Field of Classification Search
CPC .............. H04Q 9/02; H04Q 2209/40; H04Q 2209/826; H04Q 9/00; A61B 5/00
See application file for complete search history.

(56) References Cited

U.S. PATENT DOCUMENTS

| | | | |
|---|---|---|---|
| 10,154,460 B1* | 12/2018 | Miller | A61B 5/7278 |
| 2008/0243012 A1* | 10/2008 | Fujihashi | H03M 7/4006 |
| | | | 600/509 |
| 2009/0125079 A1* | 5/2009 | Armstrong | A61N 1/3605 |
| | | | 607/45 |
| 2013/0338453 A1* | 12/2013 | Duke | A61B 5/486 |
| | | | 600/309 |

(Continued)

FOREIGN PATENT DOCUMENTS

| JP | 2004-216125 A | 8/2004 |
|---|---|---|
| JP | 2018-059736 A | 4/2016 |

(Continued)

OTHER PUBLICATIONS

International Search Report for PCT/JP2017/034840 dated Nov. 28, 2017 [PCT/ISA/210].

(Continued)

*Primary Examiner* — Amine Benlagsir (57) ABSTRACT

Provided is a technique for restraining the amount of information as a whole while securing, as appropriate, information contributive to determination that utilizes a sensor. This sensor device 200 comprises: a measurement unit 210 for repeatedly measuring first information and second information which is measured at time intervals longer than those for the first information; and an output unit 220 for outputting the first information and second information measured by the measurement unit 210. When the first information and the second information meet respective standards thereof, the output unit 220 outputs the second information at longer intervals.

18 Claims, 7 Drawing Sheets

(56) References Cited

U.S. PATENT DOCUMENTS

| | | | |
|---|---|---|---|
| 2014/0121567 A1* | 5/2014 | Hasegawa | A61B 5/0024 |
| | | | 600/595 |
| 2016/0171514 A1* | 6/2016 | Frank | G06Q 30/02 |
| | | | 705/7.29 |
| 2020/0273584 A1* | 8/2020 | Bonomi | G16H 50/50 |

FOREIGN PATENT DOCUMENTS

| | | |
|---|---|---|
| JP | 2016-198193 A | 12/2016 |
| JP | 2018-538016 A | 12/2016 |
| JP | 2017-063946 A | 4/2017 |

OTHER PUBLICATIONS

Written Opinion for PCT/JP2017/034840 dated Nov. 28, 2017 [PCT/ISA/237].

* cited by examiner

SENSOR DEVICE, SENSING METHOD, AND PROGRAM STORAGE MEDIUM

CROSS-REFERENCE TO RELATED APPLICATIONS

The present application is a continuation application of U.S. patent application Ser. No. 16/650,023 filed on Mar. 24, 2020, which is a National Stage Entry of international application PCT/JP2017/034840 filed on Sep. 27, 2017, the disclosures of all of which are incorporated in their entirety by reference herein.

TECHNICAL FIELD

The present disclosure relates to a sensor device and the like.

BACKGROUND ART

There is a technique of determining a state of a target object (such as a human and a machine) by using a sensor. This type of determination may be performed by using a plurality of sensors (e.g., see PTLs 1 and 2).

CITATION LIST

Patent Literature

[PTL 1] Japanese Unexamined Patent Application Publication No. 2004-216125
[PTL 2] Japanese Unexamined Patent Application Publication No. 2017-063946

SUMMARY OF INVENTION

Technical Problem

A degree of necessity may vary among pieces of information to be acquired by sensors. Generally, a countermeasure that unnecessary information and information having a low degree of importance are not measured, or are measured but are not recorded may be required. However, there is a technical issue that information necessary for determination on a state of a target object may not be appropriately recorded when controlling a driving condition (a measurement interval or a measurement item), based on a residual amount of a battery and a measurement time of a sensor, such as a technique described in PTL 2.

In view of such an issue, an exemplary object of the present disclosure is to provide a technique for suppressing an information amount as a whole, while appropriately securing information contributive to determination using a sensor.

Solution to Problem

In one aspect, a sensor device is provided. The sensor device includes: measurement unit that repeatedly measures first information and second information, the second information being measured at a time interval which is longer than that for the first information; and an output unit that outputs the first information and the second information being measured by the measurement unit, and extends a time interval at which the second information is output when the first information and the second information satisfy, respectively, criteria associated with each of the first information and the second information.

In other aspect, another sensor device is provided, includes: measurement unit that repeatedly measures first information and second information, the second information being measured at a time interval which is longer than that of the first information; and an output unit that outputs for outputting the first information and the second information being measured by the measurement unit, and shortens a time interval at which the second information is output after at least one of the first information and the second information does not satisfy a criterion associated with it.

In other aspect, a sensing method is provided. The sensing method includes: repeatedly measuring first information and second information, the second information being measured at a time interval which is longer than that for the first information; and outputting, when the first information and the second information satisfy, respectively, criteria associated with each of the first information and the second information, the first information and the second information in such a way as to extend a time interval at which the second information is output.

In other aspect, another sensing method is provided. The sensing method includes: repeatedly measuring first information and second information, the second information being measured at a time interval which is longer than that for the first information; and outputting, after at least one of the first information and the second information does not satisfy a criterion associated with it, the first information and the second information in such a way as to shorten a time interval at which the second information is output.

In other aspect, a computer-readable program recording medium is provided. The recording medium stores a program for causing a computer to execute: repeatedly measuring first information and second information, the second information being measured at a time interval which is longer than that for the first information; and outputting the measured first information and the measured second information, and extending a time interval at which the second information is output when the first information and the second information satisfy, respectively, criteria associated with each of the first information and the second information.

In other aspect, another computer-readable program recording medium is provided. The recording medium stores a program for causing a computer to execute: repeatedly measuring first information and second information, the second information being measured at a time interval which is longer than that for the first information; and outputting the measured first information and the measured second information, and shortening a time interval at which the second information is output, after at least one of the first information and the second information does not satisfy a criterion associated with it.

Advantageous Effects of Invention

The present disclosure suppresses an information amount as a whole, while appropriately securing information contributive to determination using a sensor.

EXAMPLE EMBODIMENT

First Example Embodiment

Figure 1:
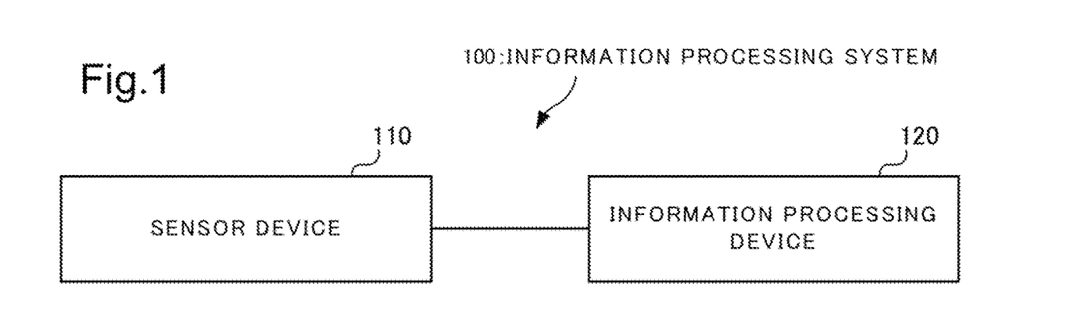
FIG. 1 is a block diagram illustrating one example of a configuration of an information processing system.

FIG. 1 is a block diagram illustrating a configuration of an information processing system 100 according to one example embodiment. The information processing system 100 includes at least a sensor device 110 and an information processing device 120. The sensor device 110 and the information processing device 120 are connected to each other via a communication network, for example.

The sensor device 110 is a device for acquiring information relating to a person being a sensing target. According to the present example embodiment, the sensor device 110 includes a plurality of sensors, and is worn on a person being a sensing target (hereinafter, also referred to as a "subject"). The sensor device 110 may be a so-called wearable device.

Herein, the information relating to a person is information derived from the person for measurement. Specifically, the information relating to a person includes at least physiological information. According to the present example embodiment, the physiological information is information indicating a physiological state of a living body to be measured via the living body. The physiological information includes, for example, a so-called vital sign (a body temperature, a respiratory rate, a blood pressure, and the like), a cardiac or muscular electrical activity (a so-called electrocardiogram and the like), an electrodermal activity, a blood oxygenation level, presence or absence of light reflex, and the like. The physiological information may be information (such as a speed and an acceleration) indicating movement of the living body (or a specific portion thereof). The physiological information may be paraphrased as physical information.

Further, the information relating to a person may include environmental information. According to the present example embodiment, the environmental information is information that indicates an environment surrounding the living body, and affects a physiological state of the living body or may change depending on the physiological state of the living body. The environmental information includes, for example, sound, brightness, a temperature, a humidity, and the like surrounding the living body. In the following, the physiological information and the environmental information according to the present example embodiment are also generically referred to as "monitoring information". The monitoring information according to the present example embodiment is information to be directly or indirectly measured from the living body, and can also be said to be information associated with the physiological state of the living body.

Figure 2:
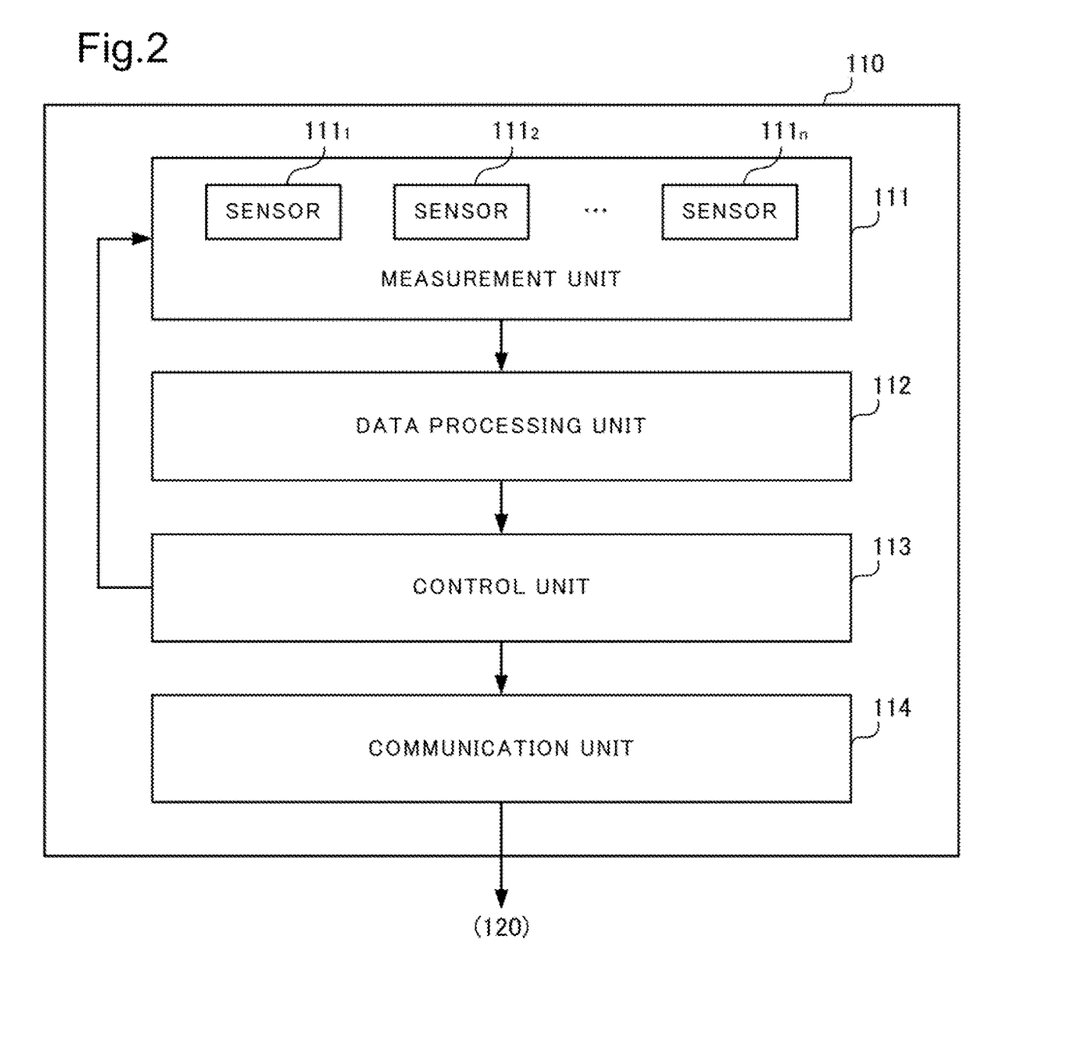
FIG. 2 is a block diagram illustrating one example of a configuration of a sensor device.

FIG. 2 is a block diagram illustrating a configuration of the sensor device 110. The sensor device 110 includes a measurement unit 111, a data processing unit 112, a control unit 113, and a communication unit 114. The sensor device 110 may further include a button and a switch for receiving an operation of a subject. Note that, in FIG. 2, the arrow in FIG. 2 illustrates one example of a flow of data. The flow of data in the sensor device 110 is not limited to the one illustrated by the arrow in FIG. 2.

The measurement unit 111 measures the monitoring information. More specifically, the measurement unit 111 includes sensors $111_1$, $111_2$, ..., and $111_n$. Herein, the number of the sensors (specifically, the value of n) may be equal to or more than 2. The sensors $111_1$ to $111_n$ are a plurality of sensors, each measuring different monitoring information. The sensors $111_1$ to $111_n$ each measure a predetermined physical amount, thereby measuring the monitoring information. The measuring unit 111 supplies the monitoring information to the data processing unit 112.

The sensors $111_1$ to $111_n$ are each configured in such a way as to be able to repeatedly measure the monitoring information. The sensors $111_1$ to $111_n$ periodically measure the monitoring information at measurement intervals determined by the control unit 113, for example. However, the measurement intervals by the sensors $111_1$ to $111_n$ may be different from one another, or may be equal to one another. The sensors $111_1$ to $111_n$ may record a time when the monitoring information is acquired together with the acquired monitoring information.

The data processing unit 112 performs predetermined processing, based on the monitoring information. The processing to be performed by the data processing unit 112 includes at least processing of determining whether the monitoring information supplied from the measuring unit 111 satisfies a predetermined criterion. The data processing unit 112 is configured to include a microcomputer (microcontroller), for example.

The criterion in determination by the data processing unit 112, specifically, determination as to whether the monitoring information satisfies the predetermined criterion differs for each piece of the monitoring information. In other words, it can also be said that the criterion in determination by the data processing unit 112 differs for each sensor. For example, the data processing unit 112 determines whether a value indicating the monitoring information lies within a predetermined numerical range. Alternatively, the data processing unit 112 may determine whether a timewise change (specifically, a waveform) of the value indicating the monitoring information matches a predetermined pattern.

The data processing unit 112 supplies data indicating a result of such a determination to the control unit 113 together with the monitoring information. For example, the data processing unit 112 supplies, to the control unit 113, data indicating a determination result by a flag "1" or "0". However, the data are not necessarily limited to the flag, as far as the data can determine whether the monitoring information satisfies the predetermined criterion.

The control unit 113 performs processing depending on a determination result by the data processing unit 112. The control unit 113 controls measurement intervals by the sensors $111_1$ to $111_n$, based on the determination result by the data processing unit 112. Further, the control unit 113 supplies, to the communication unit 114, the monitoring information supplied from the data processing unit 112. The control unit 113 is configured to include one or a plurality of processors, for example. Alternatively, the control unit 113 may be configured integrally with the data processing unit 112.

The communication unit 114 transmits, to the information processing device 120, data supplied from the control unit 113. Further, the communication unit 114 may receive data from the information processing device 120. The communication unit 114 is configured to include a communication module associated with communication with the sensor device 110 and the information processing device 120, for example.

Figure 3:
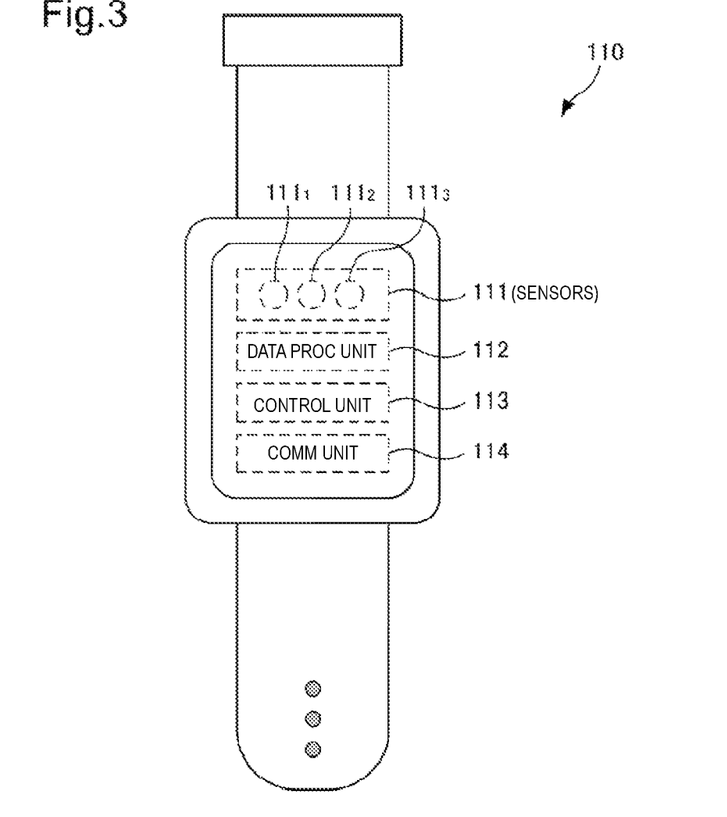
FIG. 3 illustrates one example of a form of the sensor device.

FIG. 3 illustrates one example of a form of the sensor device 110. The sensor device 110 may be a wristwatch-type wearable device as exemplified in FIG. 3. In the example of FIG. 3, the sensors $111_1$ to $111_3$ are provided in such a way as to come into contact with a subject, when being worn on the subject.

Note that the sensor device 110 is not limited to such a form, but may be a sheet-type device to be attached to the skin of a subject, for example, or may be a device integrally formed with a garment of a subject. Further, the sensor device 110 may be configured in such a way that the sensors $111_1$ to $111_n$ are wirelessly connected to a main body. In this case, the sensors $111_1$ to $111_n$ may be individually worn on a plurality of portions of a subject (a head portion, an arm portion, a chest portion, and the like).

The information processing device 120 is a computer device for monitoring a state of a subject by a guardian (e.g., a medical professional such as a doctor). The information processing device 120 is, for example, a personal computer. The information processing device 120 may be mobile equipment such as a smartphone and a tablet terminal.

Figure 4:
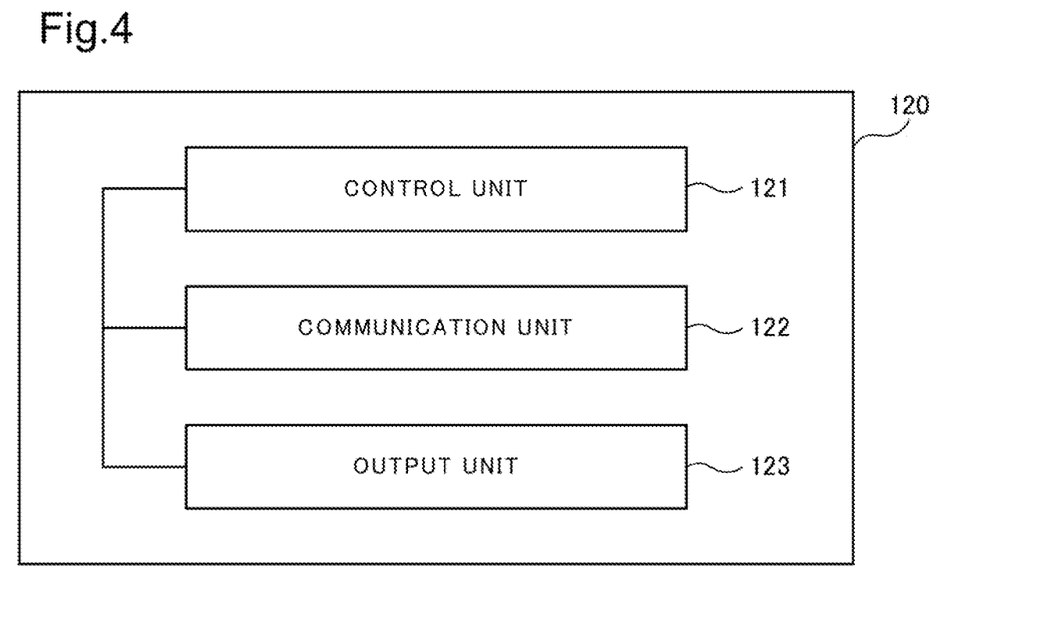
FIG. 4 is a block diagram illustrating one example of a configuration of an information processing device.

FIG. 4 is a block diagram illustrating a configuration of the information processing device 120. The information processing device 120 includes a control unit 121, a communication unit 122, and an output unit 123. Further, the information processing device 120 may include an input unit such as a mouse and a keyboard.

The control unit 121 controls an operation of each unit of the information processing device 120. For example, the control unit 121 controls an output by the output unit 123, based on data received by the communication unit 122. The control unit 121 is constituted of one or a plurality of processors, for example.

The communication unit 122 receives data transmitted from the sensor device 110. Further, the communication unit 122 may transmit data to the sensor device 110. The communication unit 122 is configured to include a communication module associated with communication with the sensor device 110 and the information processing device 120, for example. Note that the communication unit 122 may wirelessly and directly communicate with the sensor device 110, but may communicate with the sensor device 110 via another communication equipment. In such a case, the communication unit 122 may wiredly communicate with the another communication equipment.

The output unit 123 outputs information. The output herein includes, in addition to displaying to a displaying medium (such as paper and a display), electromagnetic recording to a recording medium, and sound output. Therefore, the output unit 123 may include a display or a printer for displaying the monitoring information, and may include a writing device for writing the monitoring information on a storage medium such as a hard disk. Further, the output unit 123 may include a speaker and a buzzer.

Note that, in the information processing system 100, the number of the sensor devices 110 and the information processing devices 120 is not specifically limited. For example, the information processing system 100 may include the sensor devices 110 and the information processing devices 120 by the same number (e.g., one for each device), or may be configured in such a way that many sensor devices 110 are connected to one or a few information processing devices 120.

A configuration of the information processing system 100 is as described above. In a configuration as described above, the sensor device 110 measures monitoring information of a subject who wears the sensor device 110, and transmits the measured monitoring information to the information processing device 120. Further, the information processing device 120 outputs the monitoring information.

A guardian refers to the monitoring information output by the information processing device 120, and determines a physiological anomaly of a subject. Therefore, the information processing system 100 provides the guardian with information for determining a physiological anomaly. In other words, it can also be said that the monitoring information to be provided by the information processing system 100 does not have to indicate an anomaly itself of a subject, but is only required to indicate a symptom of anomaly, in other words, a possibility of anomaly. Note that the guardian herein may be the subject himself or herself.

Figure 5:
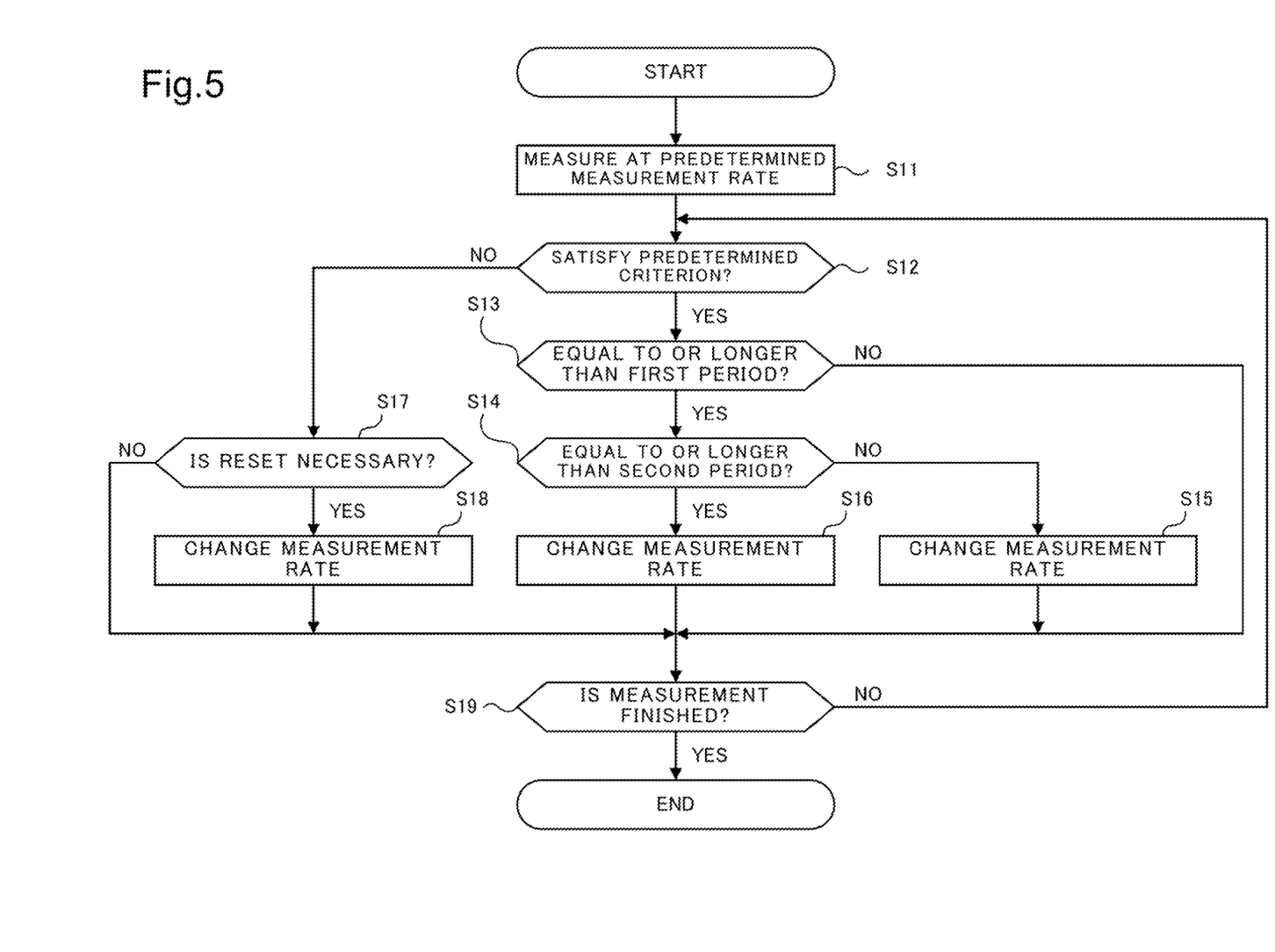
FIG. 5 is a flowchart illustrating one example of an operation of the sensor device.

FIG. 5 is a flowchart illustrating an operation of the sensor device 110. The sensor device 110 performs the following processing, when measurement by the sensors $111_1$ to $111_n$ is started. In the following, processing exemplified in FIG. 5 is also referred to as "timing control".

In Step S11, the control unit 113 causes the sensors $111_1$ to $111_n$ to perform measurement at a predetermined measurement rate. The measurement rate herein means a time interval at which the measurement unit 111 measures the monitoring information, or a time interval at which the data processing unit 112 acquires the monitoring information from the measurement unit 111. The measurement unit 111 measures the monitoring information at the measurement rate set by the control unit 113. Note that the measurement rate to be set in Step S11, specifically, an initial value of the measurement rate may differ for each of the sensors $111_1$ to $111_n$.

In Step S12, the data processing unit 112 determines whether all pieces of the monitoring information supplied from the measurement unit 111 satisfy a predetermined criterion. For example, the data processing unit 112 determines whether data indicating each piece of the monitoring information lie within a numerical range set for each piece of the monitoring information. The numerical range herein is paraphrased as an allowable range.

The data processing unit 112 notifies the control unit 113 of a time when all pieces of the monitoring information are determined to satisfy the predetermined criterion. Further, the data processing unit 112 supplies, to the control unit 113, a determination result in Step S12, specifically, data indicating whether all pieces of the monitoring information satisfy the predetermined criterion.

When all pieces of the monitoring information supplied from the measurement unit 111 satisfy the predetermined criterion (S12: YES), the control unit 113 performs Step S13. On the other hand, when at least one of the pieces of the monitoring information supplied from the measurement unit 111 does not satisfy the predetermined criterion (S12: NO), the control unit 113 performs Step S17.

In Step S13, the control unit 113 determines whether a period during which all pieces of the monitoring information satisfy the predetermined criterion is equal to or longer than a predetermined period (hereinafter, also referred to as a "first period"). Although the first period is not specifically limited, the first period is, for example, "three minutes" and the like. The control unit 113 may determine whether a period during which all pieces of the monitoring information satisfy the predetermined criterion is equal to or longer than the predetermined period, at a time when Step S13 is performed, by using a time when the monitoring information is acquired, for example. The control unit 113 may determine, from the measurement rate, whether the period during which all pieces of the monitoring information satisfy the predetermined criterion is equal to or longer than the predetermined period. When the period during which all pieces of the monitoring information satisfy the predetermined criterion is equal to or longer than the first period (S13: YES), the control unit 113 performs Step S14.

On the other hand, when the period during which all pieces of the monitoring information satisfy the predetermined criterion is shorter than the first period (S13: NO), the data processing unit 112 performs Step S19. Specifically, in this case, the control unit 113 does not change the measurement rate.

In Step S14, the control unit 113 determines whether the period during which all pieces of the monitoring information satisfy the predetermined criterion is equal to or longer than another predetermined period (hereinafter, also referred to as a "second period"). The second period is set longer than the first period in Step S13. The second period is, for example, "five minutes" and the like.

When the period during which all pieces of the monitoring information satisfy the predetermined criterion is equal to or longer than the second period (S14: YES), the control unit 113 performs Step S16. On the other hand, when the period during which all pieces of the monitoring information satisfy the predetermined criterion is shorter than the second period (not shorter than the first period but shorter than the second period) (S14: NO), the control unit 113 performs Step S15.

In Steps S15 and S16, the control unit 113 changes at least one of the measurement rates of the sensors $111_1$ to $111_n$. Steps S15 and S16 are common in a point that the step is processing of changing the measurement rate. On the other hand, Steps S15 and S16 are different in measurement rate after changing. Specifically, when the measurement rates of the sensors $111_1$ to $111_n$ are compared between after Step S15 is performed and after Step S16 is performed, at least one of the measurement rates is not identical.

More specifically, in Step S15, the control unit 113 changes at least one of the measurement rates of the sensors $111_1$ to $111_n$ in such a way as to extend the time interval at which the monitoring information is measured. In this case, the measurement rate is set to a predetermined time interval longer than that in a case of the first period, when a time reaches the second period after completion of the first period. Further, in Step S16, the control unit 113 changes at least one of the measurement rates of the sensors $111_1$ to $111_n$ in which the measurement rate is changed in Step S15 in such a way as to further extend the time interval at which the monitoring information is measured.

Processing of Steps S13 to S16 is processing in a case that all pieces of the monitoring information satisfy the predetermined criterion. In contrast, processing of Steps S17 to S18 is processing in a case that at least one piece of the monitoring information does not satisfy the predetermined criterion. Processing of Steps S17 to S18 can be said to be processing of resetting (specifically, returning to the initial value) the measurement rate changed by processing of Steps S13 to S16.

In Step S17, the control unit 113 determines whether it is necessary to reset the measurement rate. Specifically, the control unit 113 determines whether the measurement rate is an initial value regarding a sensor in which the measurement rate is reset in Step S18. When the measurement rate is kept to the initial value, specifically, remains unchanged, the control unit 113 determines that resetting the measurement rate is not necessary. In this case (S17: NO), the control unit 113 skips Step S18.

On the other hand, when the measurement rate is changed from the initial value (S17: YES), the control unit 113 performs Step S18. In Step S18, the control unit 113 resets at least one of the measurement rates changed by processing of Steps S13 to S16. The control unit 113 may return all the measurement rates changed by processing of Steps S13 to S16 to the initial value, or may return only the measurement rate of a predetermined piece of the monitoring information to the initial value.

In Step S19, the control unit 113 determines whether to finish measurement of the monitoring information by the measurement unit 111. For example, when the period during which the monitoring information is measured reaches equal to or more than a predetermined threshold value, the control unit 113 finishes measurement of the monitoring information. Further, the control unit 113 may finish measurement of the monitoring information, when a predetermined time has come. Alternatively, the control unit 113 may finish measurement of the monitoring information in response to an instruction from the information processing device 120 or an operation of a subject.

Figure 6:
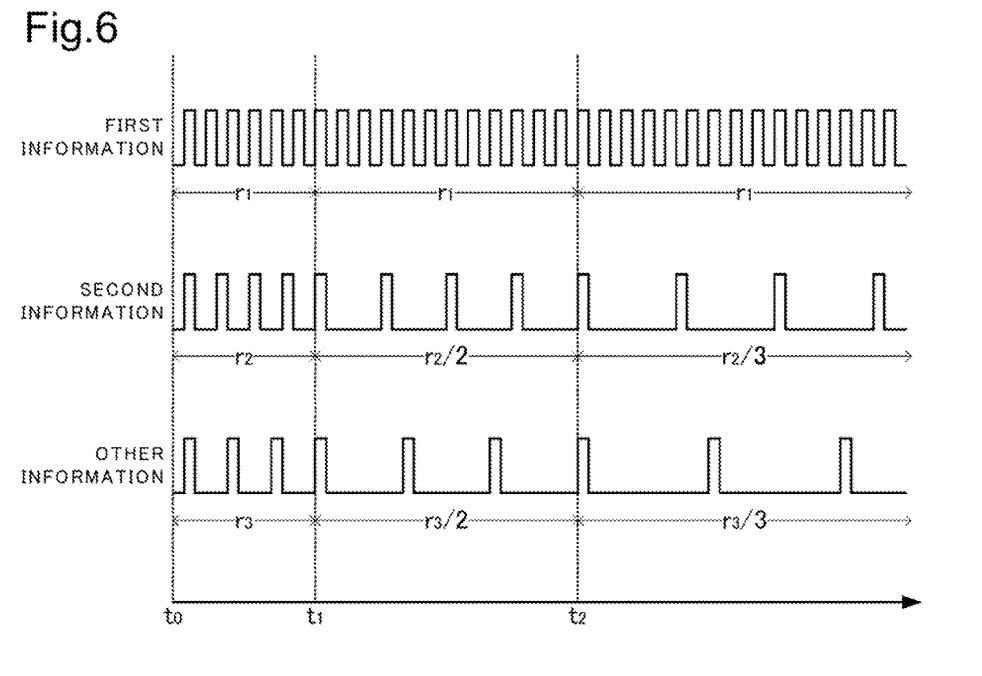
FIG. 6 is a timing chart illustrating a first example of transition of a measurement rate.
Figure 7:
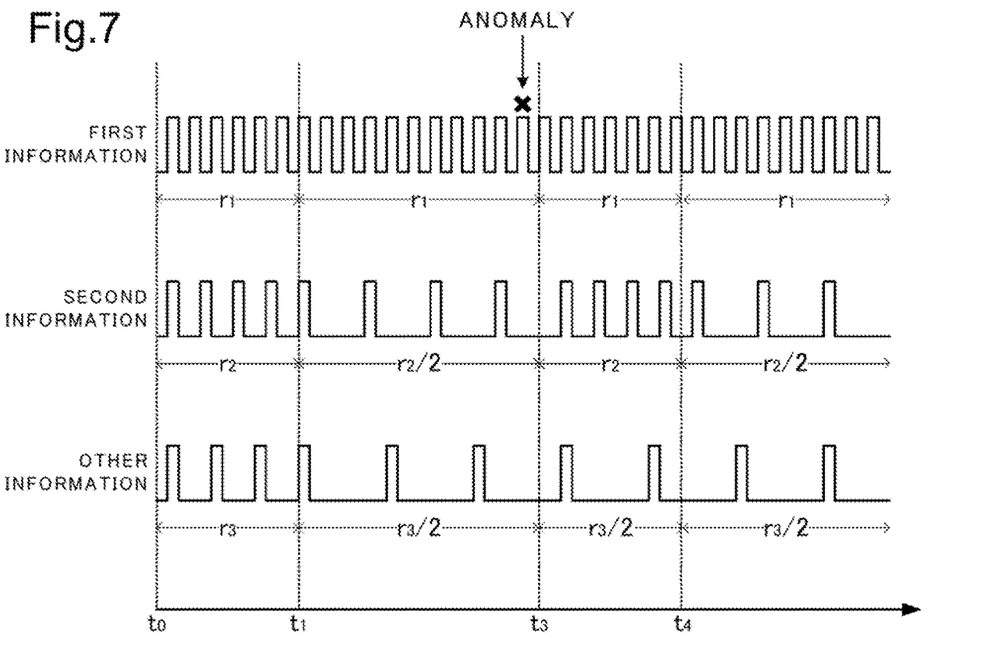
FIG. 7 is a timing chart illustrating a second example of the transition of the measurement rate.
Figure 8:
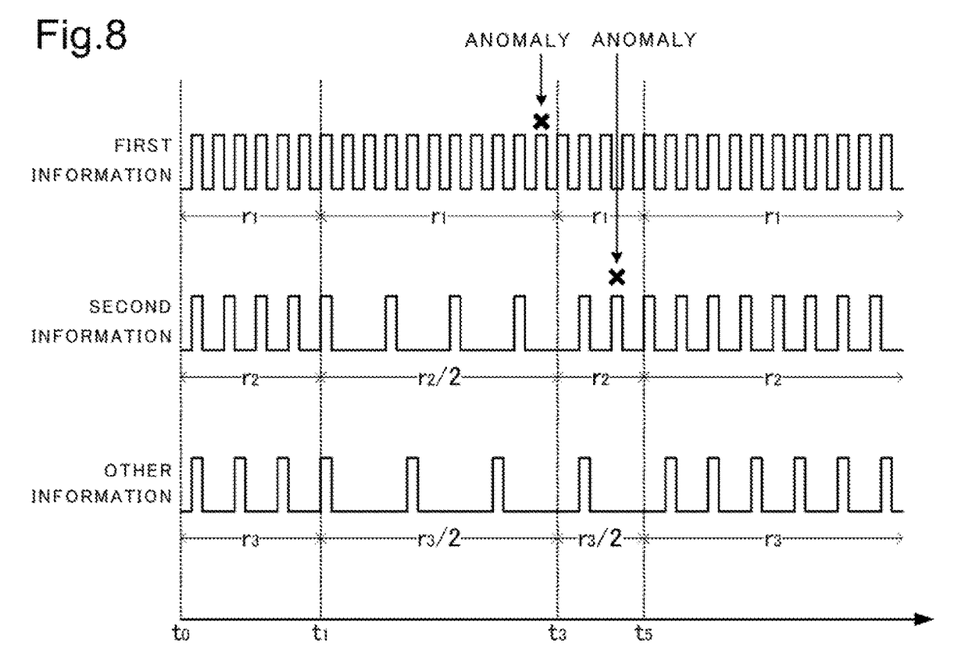
FIG. 8 is a timing chart illustrating a third example of the transition of the measurement rate.

FIGS. 6 to 8 are timing charts exemplifying transition of a measurement rate. The timing chart of FIG. 6 illustrates a change in measurement rate, when there is no anomaly in monitoring information. The timing charts of FIGS. 7 and 8 illustrate a change in measurement rate, when some anomaly has occurred in the monitoring information. These timing charts illustrate a timing at which the monitoring information is acquired by a signal indicating one of two levels. The monitoring information is acquired at a timing when the signal reaches a high level (specifically, turns on).

Note that an anomaly in monitoring information herein indicates a state that the monitoring information does not satisfy a predetermined criterion. Therefore, even when there is an anomaly in monitoring information, this does not directly mean that there is a physiological anomaly in a subject. In other words, an anomaly in monitoring information merely suggests that there may be a physiological anomaly in the subject.

Further, in this example, the monitoring information is classified into "first information", "second information", and "other information". Herein, the first information is monitoring information in which an influence given to determination on a physiological anomaly of the subject is largest. The second information is monitoring information in which an influence given to determination on a physiological anomaly of the subject is second largest to the first information. The other information is one or a plurality of pieces of monitoring information in which an influence given to determination on a physiological anomaly of the subject is small, as compared with the first information and the second information, but contributes to anomaly determination. However, the other information is not essentially required in the present example embodiment, and does not need to be included in the monitoring information.

According to the present example embodiment, the first information is measured at a shorter time interval than that for the other monitoring information. The second information is measured at a time interval longer than that for the first information but shorter than that for the other information. The other monitoring information is measured at a longer time interval than those for the first information and the second information. Therefore, a frequency with which these pieces of information are measured per unit time is highest in the first information, and lowest in the other information.

Note that, herein, it is assumed that an initial value of the measurement rate of the first information is $r_1$, an initial value of the measurement rate of the second information is $r_2$, and an initial value of the measurement rate of the other information is $r_3$. $r_1$, $r_2$, and $r_3$ indicate the number of times of acquisition of monitoring information per unit time (e.g., one minute), and $r_1 > r_2 > r_3$ is satisfied herein.

In FIG. 6, a period from a time $t_0$ to a time $t_1$ corresponds the first period. Further, a period from the time $t_0$ to a time $t_2$ corresponds to the second period. In FIG. 6, during the first period, there is no anomaly in all pieces of the monitoring information (specifically, a predetermined criterion is satisfied). Therefore, the control unit 113 changes the measurement rates of the second information and the other information in a period after the time $t_1$. This change in measurement rate is performed because it is determined "YES" in Steps S12 and S13, it is determined "NO" in Step S14, and Step S15 is performed in the flowchart of FIG. 5.

Further, in FIG. 6, there is no anomaly in any of the pieces of the monitoring information until the time $t_2$. Therefore, the control unit 113 further changes the measurement rates of the second information and the other information in a period after the time $t_2$. This change in measurement rate is performed because it is determined "YES" in Steps S12, S13, and S14, and Step S16 is performed in the flowchart of FIG. 5.

The measurement rate of the second information is "$r_2/2$" in a period from the time $t_1$ to the time $t_2$, specifically, one-half of the initial value, and is "$r_2/3$" in a period after the time $t_2$, specifically, one-third of the initial value. Further, the measurement rate of the other information is "$r_3/2$" in a period from the time $t_1$ to the time $t_2$, specifically, one-half of the initial value, and is "$r_3/3$" in a period after the time $t_2$, specifically, one-third of the initial value.

Note that the first information gives a large influence on determination on a physiological anomaly of a subject, as compared with the other monitoring information. Specifically, it can also be said that the first information is monitoring information to be monitored most carefully by a guardian. Therefore, according to the present example embodiment, the measurement rate of the first information is constant. In other words, the first information is set in such a way that the measurement rate does not decrease.

In FIG. 7, a period from the time $t_0$ to the time $t_1$ corresponds to the first period similarly to the example in FIG. 6. Further, an operation of changing the measurement rate at the time $t_1$ is similar to the example in FIG. 6. However, the example in FIG. 7 is different from the example in FIG. 6 in a point that an anomaly has occurred in the first information before the time reaches the time $t_2$. In this case, after the first information does not satisfy the predetermined criterion, specifically, in a period after a time $t_3$, the control unit 113 changes (specifically, resets) the measurement rate of the second information from "$r_2/2$" to "$r_2$". However, the control unit 113 does not reset the measurement rate of the other information.

Further, in FIG. 7, a period from the time $t_3$ to a time $t_4$ is a length of time correspond to the first period, and is equal to the period from the time $t_0$ to the time $t_1$. It is assumed that there is no anomaly in any of the pieces of the monitoring information during this period. In this case, the control unit 113 changes again the measurement rate of the second information from "$r_2$" to "$r_2/2$" at the time $t_4$.

FIG. 8 illustrates an example of a case that a plurality of anomalies have occurred in the monitoring information within a short period. In this example, it is assumed that an operation in a period from the time $t_0$ to the time $t_3$ is similar to the example in FIG. 7. However, the example in FIG. 8 is different from the example in FIG. 7 in a point that, after the measurement rate of the second information is reset at the time $t_3$, an anomaly has occurred in the second information before the first period lapses.

In this case, after the second information does not satisfy the predetermined criterion, specifically, in a period after a time $t_5$, the control unit 113 changes (specifically, resets) the measurement rate of the other information from "$r_3/2$" to "$r_3$". Specifically, in this example, the measurement rate of any of the pieces of the monitoring information becomes the initial value in a period after the time $t_5$. Thus, it becomes possible to determine an anomaly of the subject at an earlier stage or more securely, as compared with the case of the example in FIG. 7.

The following combination is proposed, as a combination of an anomaly of a subject and monitoring information to be monitored, to which the information processing system 100 according to the present example embodiment is applicable. For example, it is possible to apply the information processing system 100 to monitoring of a disturbed state or a problematic behavior of a patient affected by cerebral infarction by monitoring an acceleration of a specific portion (e.g., an arm portion), a heart rate, sound (mumbling), a body temperature, an electrodermal activity, a blood pressure, and the like of the subject. In this case, the acceleration may be used as the first information, and the heart rate may be used as the second information.

Further, by monitoring a heart rate, a blood oxygenation level, a blood pressure, a body temperature, a respiratory rate, and the like of the subject, it is possible to apply the information processing system 100 to monitoring of the subject when playing sports such as mountain climbing and running. In this case, the heart rate may be used as the first information, and the blood oxygenation level may be used as the second information.

Further, by monitoring an acceleration of a specific portion, a heart rate, a respiratory rate, a body temperature, a blood pressure, sound, and the like of the subject, it is possible to apply the information processing system 100 to confirmation on safety or watching support of elderly people living alone. For example, by using the acceleration as the first information, and the respiratory rate as the second information, it is possible to detect falling in a bathroom and the like. Alternatively, by using the heart rate as the first information, and the respiratory rate as the second information, it is possible to detect a symptom of a cardiac disease.

As described above, the information processing system 100 according to the present example embodiment includes a configuration in which timing control depending on a measurement result of monitoring information is performed. This configuration enables widening, when there is no anomaly in all pieces of the monitoring information to be measured, a measurement interval of monitoring information, and narrowing, when there is an anomaly in at least one of the pieces of the monitoring information to be measured, the measurement interval of the monitoring information.

Generally, when monitoring information stably satisfies a predetermined criterion, it can be said that a possibility with which an anomaly has occurred in a subject is low. In such a case, the information processing system 100 can widen the measurement interval of the monitoring information. On the other hand, when monitoring information that does not satisfy the predetermined criterion is detected, more detailed or finer determination is requested to a guardian. In such a case, the information processing system 100 can narrow the measurement interval of the monitoring information.

Therefore, the information processing system 100 can narrow, when a close inspection of the monitoring information is required, the measurement interval of monitoring information, and widen, when a close inspection is not required, the measurement interval of the monitoring information. Thus, the information processing system 100 enables suppressing an information amount as a whole, while appropriately securing information contributive to determination using a sensor. In other words, the information processing system 100 enables providing both of an advantageous effect of appropriately securing information contributive to determination using a sensor, and an advantageous effect of suppressing an information amount as a whole.

Further, when the measurement interval of monitoring information is constant, a long measurement interval of a certain piece of monitoring information means that an anomaly has not occurred in the monitoring information for a certain period. Conversely, a short measurement interval of a certain piece of monitoring information even after a lapse of a certain period means that some anomaly has occurred in the monitoring information. In this way, the information processing system 100 according to the present example embodiment enables providing an accompanying advantageous effect that a guardian can easily capture presence or absence of an anomaly in a latest piece of monitoring information by the measurement interval of monitoring information at a certain time.

Second Example Embodiment

Figure 9:
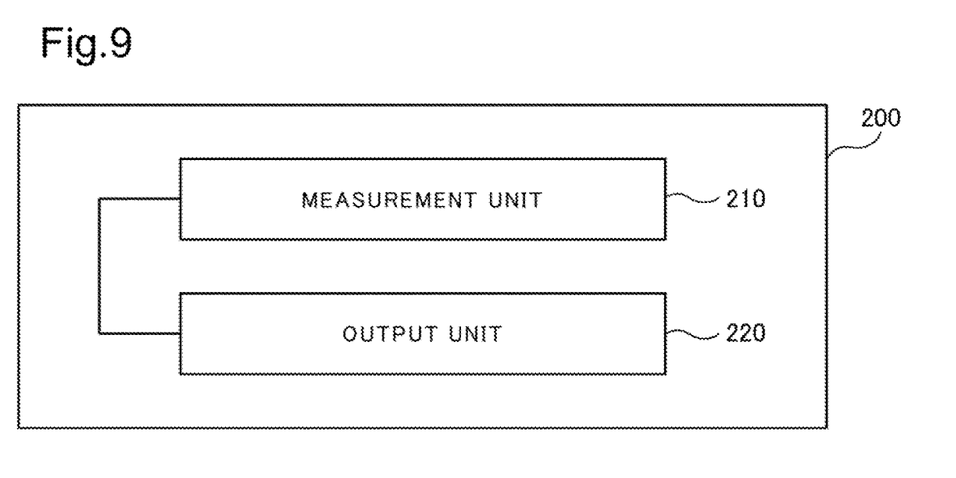
FIG. 9 is a block diagram illustrating another example of a configuration of the sensor device.

FIG. 9 is a block diagram illustrating a configuration of a sensor device 200 according to another example embodiment. The sensor device 200 includes at least a measurement unit 210 and an output unit 220. The sensor device 110 according to the first example embodiment corresponds to one example of the sensor device 200.

The measurement unit 210 repeatedly measures a plurality of pieces of information. For example, the measurement unit 210 measures the plurality of pieces of information at a predetermined time interval. The time interval at which each piece of the information is measured by the measurement unit 210 does not need to be limited to a specific numerical range.

According to the present example embodiment, the measurement unit 210 measures equal to or more than two pieces of information. The time interval differ in each piece of the information is measured. In the following, among a plurality of pieces of information to be measured by the measurement unit 210, information having a shortest time interval at which the information is measured is also referred to as "first information", and information having a time interval at which the information is measured longer than that for the first information is also referred to as "second information".

Information to be measured by the measurement unit 210 according to the present example embodiment may include the monitoring information according to the first example embodiment. However, the information to be measured by the measurement unit 210 according to the present example embodiment is not limited to the monitoring information. Further, a sensing target according to the present example embodiment is not necessarily a person, but may be another living being or a machine. Furthermore, the sensing target according to the present example embodiment may be soil, liquid, gas, and the like.

The measurement unit 210 may include one or more sensors, and may include an interface for acquiring information from the one or more sensors. In other words, the measurement unit 210 may not necessarily include a sensor itself. Therefore, the measurement unit 210 may have a configuration similar to that of the measurement unit 111 according to the first example embodiment, but is not limited to only such a configuration.

The output unit 220 outputs the plurality of pieces of information measured by the measurement unit 210. The time interval at which the plurality of pieces of information are output by the output unit 220 may change by determination as to whether each of the time intervals satisfies a predetermined criterion, or depending on a length of time during which the criterion is satisfied. The data processing unit 112 and the control unit 113 according to the first example embodiment corresponds to one example of the output unit 220.

In a first mode, the output unit 220 extends, when the first information and the second information satisfy each of criteria, a time interval at which the second information is output. Specifically, the time interval at which the second information is output is extended, when the first information and the second information satisfy each of the criteria, as compared with a case that the first information and the second information do not satisfy each of the criteria. For example, when the first information and the second information satisfy each of the criteria over a predetermined period, the output unit 220 extends the time interval at which the second information is output.

In a second mode, the output unit 220 shortens, after at least one of the first information and the second information does not satisfy each of the criteria, the time interval at which the second information is output. Specifically, after the first information and the second information do not satisfy each of the criteria, the time interval at which the second information is output is shortened, as compared with a period until the first information and the second information satisfy each of the criteria. For example, after the first information and the second information satisfy each of the criteria over a predetermined period, the output unit 220 shortens, when at least one of the first information and the second information does not satisfy the criterion, the time interval at which the second information is output.

The output unit 220 operates in at least one of a first mode and a second mode. Further, the output unit 220 may operate by combining the first mode and the second mode. For example, the data processing unit 112 and the control unit 113 according to the first example embodiment contributes to combination of the first mode and the second mode.

In some of the cases, the output unit 220 enables controlling a time interval at which information is output by controlling a measurement interval of information by the measurement unit 210, such as the control unit 113 according to the first example embodiment. However, the output unit 220 also enables controlling a time interval at which information is output without changing a measurement interval of information by the measurement unit 210.

For example, the output unit 220 may thin out at least a part of information measured by the measurement unit 210 and output the remaining information. More specifically, when the second information is measured i times per unit time, the output unit 220 outputs the second information of an amount equivalent to j times out of i times, and discards the second information of an amount equivalent to (i−j) times. Herein, j satisfies: i>j.

The output unit 220 may control a time interval at which the other information is output, in addition to the second information or in place of the second information. For example, the output unit 220 may control the time interval at which the first information is output, in addition to the second information. Alternatively, the output unit 220 may control the time interval at which third information is output, in place of the second information. Herein, the third information is, among a plurality of pieces of information to be measured by the measurement unit 210, information having a time interval at which the information is measured longer than that for the first information, and not being the second information. For example, "the other information" according to the first example embodiment corresponds to one example of the third information.

For example, when the first information, the second information, and the third information satisfy each of criteria, the output unit 220 may extend the time interval at which at least one of the second information and the third information is output. Alternatively, when the first information, the second information, and the third information satisfy each of criteria, the output unit 220 may extend the time interval at which the first information, the second information, and the third information are output.

Further, the output unit 220 may shorten, after the first information does not satisfy a criterion, the time interval at which the second information is output, and may shorten, after the second information does not satisfy a criterion, the time interval at which the second information and the third information are output (e.g., see FIG. 8).

Alternatively, the output unit 220 may shorten, when the number of times that the first information, the second information, or the third information does not satisfy a criterion is smaller than a predetermined frequency, the time interval at which the second information is output, and may shorten, when the number of times is equal to or larger than the predetermined frequency, the time interval at which the second information and the third information are output. It can also be said that the frequency herein is the number of times of occurrence of anomaly in the first information, the second information, or the third information within a predetermined time. It can also be said that the example in FIG. 8 is an example of a case that the predetermined frequency herein is set to "two (times)".

Figure 10:
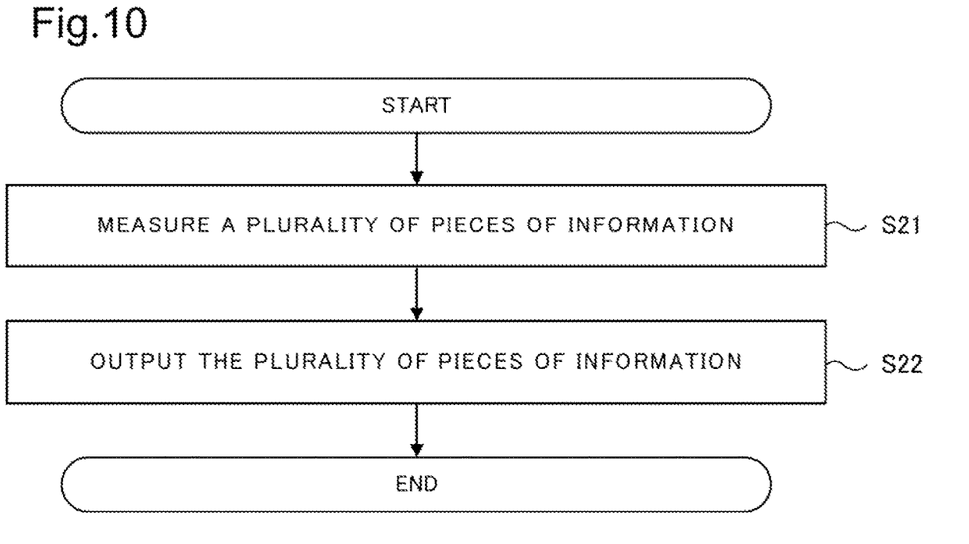
FIG. 10 is a flowchart illustrating one example of an operation of the sensor device.

FIG. 10 is a flowchart illustrating an operation of the sensor device 200. In Step S21, the measurement unit 210 measures a plurality of pieces of information at a predetermined time interval. In Step S22, the output unit 220 outputs the plurality of pieces of information measured in Step S21.

In Step S22, when the plurality of pieces of information measured in Step S21 satisfy a criterion relating to each piece of the information, the output unit 220 may extend the time interval at which one of the plurality of pieces of information (e.g., the second information) is output. Alternatively, after at least one of the plurality of pieces of information measured in Step S21 does not satisfy a criterion relating to each piece of the information, the output unit 220 may shorten the time interval at which one of the plurality of pieces of information (e.g., the second information) is output.

As described above, the sensor device 200 according to the present example embodiment includes a configuration in which control depending on a measurement result of a plurality of pieces of information is performed. This configuration enables widening, when there is no anomaly in both of the first information and the second information, the time interval at which the second information is output, and narrowing, when there is an anomaly in at least one of the first information and the second information, the time interval at which the second information is output. Therefore, similarly to the information processing system 100 according to the first example embodiment, the sensor device 200 enables suppressing an information amount as a whole, while appropriately securing information contributive to determination using a sensor.

Modification Examples

The following modifications can be applied to the above-described first and second example embodiments, for example. These modification examples may also be combined appropriately as necessary. Further, a modification example described by using a specific example embodiment may also be applied to another example embodiment, as far as contradiction does not occur.

(1) When there is an anomaly in monitoring information, the control unit 113 may output data indicating the anomaly in the monitoring information. In this case, the sensor device 110 transmits, to the information processing device 120, data indicating the anomaly in the monitoring information. The information processing device 120 may output a warning by a speaker and the like by using the data.

(2) The control unit 113 may output display data for displaying the monitoring information, in place of the monitoring information itself. In this case, the sensor device 110 transmits the display data to the information processing device 120. The information processing device 120 may display the monitoring information by using the display data.

(3) The sensor device 110 is not necessarily worn on a subject. The sensor device 110 may be configured in such a way as to measure the monitoring information without coming into contact with the subject, for example, by remotely measuring the monitoring information.

(4) A specific hardware configuration of a device according to the present disclosure (the sensor device 110, the information processing device 120, and the sensor device 200) may include various variations, and is not limited to a specific configuration. For example, a device according to the present disclosure may be achieved by using software, or may be configured in such a way that various processing is distributively performed by using a plurality of pieces of hardware.

Figure 11:
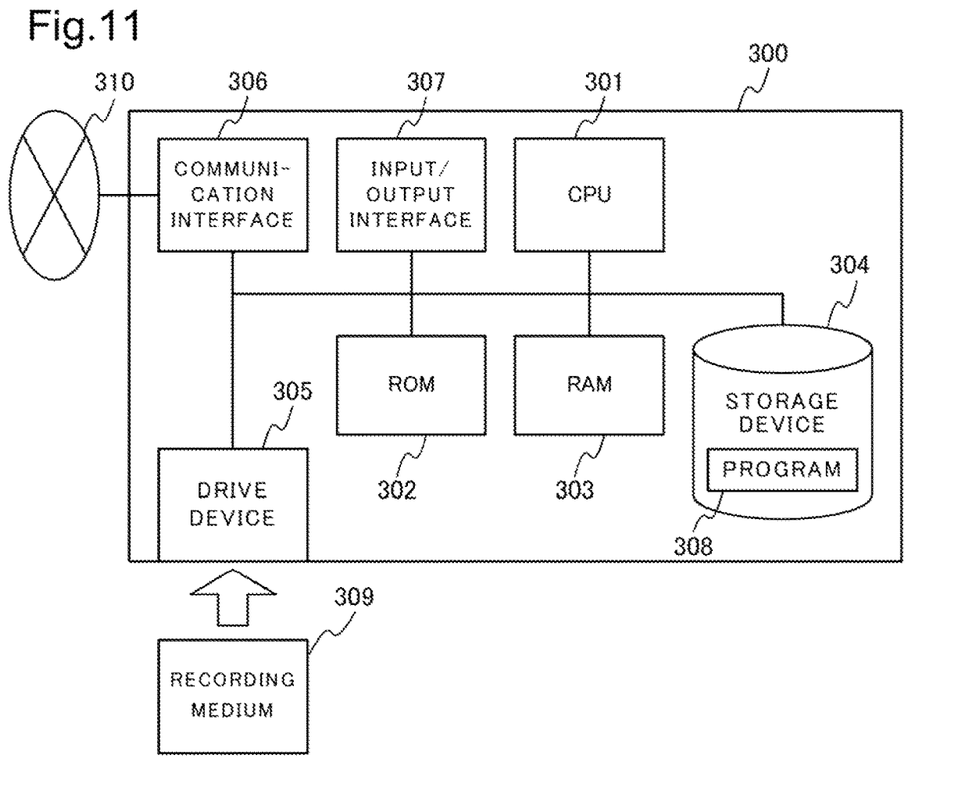
FIG. 11 is a block diagram illustrating one example of a hardware configuration of a computer device.

FIG. 11 is a block diagram illustrating one example of a hardware configuration of a computer device 300 for achieving a device according to the present disclosure. The computer device 300 is configured to include a central processing unit (CPU) 301, a read only memory (ROM) 302, a random access memory (RAM) 303, a storage device 304, a drive device 305, a communication interface 306, and an input/output interface 307.

The CPU 301 executes a program 308 by using the RAM 303. The communication interface 306 transmits and receives data to and from an external device via a network 310. The input/output interface 307 transmits and receives data to and from peripheral equipment (such as a camera, a microphone, and another sensor). The communication interface 306 and the input/output interface 307 can function as constituent elements for acquiring or outputting data.

Note that the program 308 may be stored in the ROM 302. Further, the program 308 may be recorded in a recording medium 309 such as a memory card, read by the drive device 305, and transmitted from an external device via the network 310.

A device according to the present disclosure may be achieved by a configuration (or a part thereof) illustrated in FIG. 11. For example, in a case of the sensor device 200, the measurement unit 210 and the output unit 220 are associated with the CPU 301, the ROM 302, and the RAM 303.

Note that constituent elements of a device according to the present disclosure may be configured by a single circuitry (such as a processor), or may be configured by combining a plurality of circuitries. A circuitry herein may be a dedicated or general-purpose circuitry. For example, a part of a device according to the present disclosure may be achieved by a dedicated processor, and the other part thereof may be achieved by a general-purpose processor. For example, the data processing unit 112 and the control unit 113 may be configured by a single processor, or may be configured by different processors.

[Supplementary Notes]

A part or all of the present disclosure may be described as the following supplementary notes. The present invention, however, is not necessarily limited to aspects of the supplementary notes.

(Supplementary Note 1)

A sensor device includes:
  a measurement unit that repeatedly measures first information and second information, the second information being measured at a time interval which is longer than that for the first information; and
  an output unit that outputs the first information and the second information being measured by the measurement unit, and extends a time interval at which the second information is output when the first information and the second information satisfy, respectively, criteria associated with each of the first information and the second information.

(Supplementary Note 2)

In the sensor device according to supplementary note 1, the output unit changes the time interval at which the second information is output depending on a length of time during which the first information and the second information satisfy each of the criteria.

(Supplementary Note 3)

In the sensor device according to supplementary note 1, the output unit extends, when the first information and the second information satisfy each of the criteria, a time interval at which the first information is output and the time interval at which the second information is output.

(Supplementary Note 4)

In the sensor device according to supplementary note 1, the measurement unit repeatedly measures third information being measured at a time interval which is longer than that for the first information, and the output unit extends at least one of the time interval at which the second information is output and a time interval at which the third information is output, when the first information, the second information, and the third information satisfy, respectively, criteria associated with each of the second information and the third information.

(Supplementary Note 5)

A sensor device includes:
  measurement unit that repeatedly measures first information and second information, the second information being measured at a time interval which is longer than that of the first information; and
  an output unit that outputs the first information and the second information being measured by the measurement unit, and shortenines a time interval at which the second information is output after at least one of the first information and the second information does not satisfy a criterion associated with it.

(Supplementary Note 6)

In the sensor device according to supplementary note 5, the output unit shortens, after the first information does not satisfy the criterion, a time interval at which the first information is output and the time interval at which the second information is output.

(Supplementary Note 7)

In the sensor device according to supplementary note 5, the measurement unit repeatedly measures third information being measured at a time interval which is longer than that for the first information, and the output unit shortens at least one of the time interval at which the second information is output and a time interval at which the third information is output, after at least one of the first information, the second information, and the third information does not satisfy the criterion associated with it.

(Supplementary Note 8)

In the sensor device according to supplementary note 7, the output unit shortens the time interval at which the second information is output after the first information does not satisfy the criterion, and shortens the time interval at which the second information is output and the time interval at which the third information is output after the second information does not satisfy the criterion associated with it.

(Supplementary Note 9)

In the sensor device according to supplementary note 7, the output unit shortens the time interval at which the second information is output when a number of times that the first information, the second information, or the third information does not satisfy the criterion is smaller than a predetermined frequency, and shortens the time interval at which the second information and the time interval at which the third information is output when the number of times is equal to or larger than a predetermined frequency.

(Supplementary Note 10)

The sensor device according to any one of supplementary notes 1 to 9, further includes
  a control unit controls the time interval for measurement by the measurement unit.

(Supplementary Note 11)

In the sensor device according to any one of supplementary notes 1 to 3, and supplementary notes 5 to 6,
  the output unit thins out a part of a plurality of pieces of the first information and a plurality of pieces of the second information being measured by the measurement unit and outputs the remaining information.

(Supplementary Note 12)

A sensing method includes:

repeatedly measuring first information and second information, the second information being measured at a time interval which is longer than that for the first information; and outputting, when the first information and the second information satisfy, respectively, criteria associated with each of the first information and the second information, the first information and the second information in such a way as to extend a time interval at which the second information is output.

(Supplementary Note 13)

A sensing method includes:

repeatedly measuring first information and second information, the second information being measured at a time interval which is longer than that for the first information; and outputting, after at least one of the first information and the second information does not satisfy a criterion associated with it, the first information and the second information in such a way as to shorten a time interval at which the second information is output.

(Supplementary Note 14)

A computer-readable program recording medium stores a program.

The program causes a computer to execute:

repeatedly measuring first information and second information, the second information being measured at a time interval which is longer than that for the first information; and outputting the measured first information and the measured second information, and extending a time interval at which the second information is output when the first information and the second information satisfy, respectively, criteria associated with each of the first information and the second information.

(Supplementary Note 15)

A computer-readable program recording medium stores a program.

The program causes a computer to execute:

repeatedly measuring first information and second information, the second information being measured at a time interval which is longer than that for the first information; and outputting the measured first information and the measured second information, and shortening a time interval at which the second information is output, after at least one of the first information and the second information does not satisfy a criterion associated with it.

In the foregoing, the present invention has been described by the above-described example embodiments as an exemplary example. The present invention, however, is not limited to the above-described example embodiments. Specifically, the present invention may include various aspects comprehensible to a person skilled in the art within the scope of the present invention.

REFERENCE SIGNS LIST

100 Information processing system
110 Sensor device
111 Measurement unit
112 Data processing unit
113 Control unit
114 Communication unit
120 Information processing device
121 Control unit
122 Communication unit
123 Output unit
200 Sensor device
210 Measurement unit
220 Output unit
300 Computer device

The invention claimed is:

1. A sensor device comprising:

a memory; and at least one processor coupled to the memory, the at least one processor performing operations to:

repeatedly measure first information of a user at a first time interval such that the first information is measured every time a time difference between a current time and a most recent time the first information was measured is equal to the first time interval;

repeatedly measure second information of the user at a second time interval such that the second information is measured every time a time difference between the current time and a most recent time the second information was measured is equal to the second time interval, the second information being a different kind of information than the first information is; and adjust at least one of the first time interval at which the first information is repeatedly measured and the second time interval at which the second information is repeatedly measured depending on the first information and the second information.

2. The sensor device according to claim 1, wherein the at least one processor further performs the operations to:

change at least one of the first time interval at which the first information is repeatedly measured and the second time interval at which the second information is repeatedly measured, when the first information satisfies a first criterion associated with the first information and the second information satisfies a second criterion associated with the second information.

3. The sensor device according to claim 2, wherein the at least one processor further performs the operations to:

lengthen, when the first information satisfies the first criterion and the second information satisfies the second criterion, the at least one of the first time interval at which the first information is repeatedly measured and the second time interval at which the second information is repeatedly measured.

4. The sensor device according to claim 2, wherein the at least one processor further performs the operations to:

shorten the second time interval at which the second information is repeatedly measured, when the first information does not satisfy the first criterion.

5. The sensor device according to claim 2, wherein the at least one processor further performs the operations to:

shorten the second time interval at which the second information is output according to a frequency at which the first information does not satisfy the first criterion and the second information does not satisfy the second criterion.

6. The sensor device according to claim 1, wherein the second time interval at which the second information is measured is longer than the first time interval at which the first information is measured.

7. The sensor device according to claim 1, wherein the at least one processor further performs the operations to:

shorten the at least one of the first time interval at which the first information is measured and the second time interval at which the second information is measured when the first information does not satisfy a first criterion or when the second information does not satisfy a second criterion.

8. The sensor device according to claim 1, wherein the at least one processor further performs the operations to:
change the first time interval at which the first information is measured by selectively removing measurements of the first information; and
change the second time interval at which the second information is measured by selectively removing measurements of the second information.

9. The sensor device according to claim 1, wherein the at least one processor further performs the operations to:
display at least one of the first information and the second information on display device based on the first time interval at which the first information is measured and the second time interval at which the second information is measured.

10. A sensing method comprising:
by at least one processor,
repeatedly measuring first information of a user at a first time interval such that the first information is measured every time a time difference between a current time and a most recent time the first information was measured is equal to the first time interval;
repeatedly measuring second information of the user at a second time interval such that the second information is measured every time a time difference between the current time and a most recent time the second information was measured is equal to the second time interval, the second information being a different kind of information than the first information is; and
adjusting at least one of the first time interval at which the first information is repeatedly measured and the second time interval at which the second information is repeatedly measured depending on the first information and the second information.

11. The sensing method according to claim 10, further comprising:
changing at least one of the first time interval at which the first information is repeatedly measured and the second time interval at which the second information is repeatedly measured, when the first information satisfies a first criterion associated with the first information and the second information satisfies a second criterion associated with the second information.

12. The sensing method according to claim 11, further comprising:
lengthening, when the first information satisfies the first criterion and the second information satisfies the second criterion, the at least one of the first time interval at which the first information is repeatedly measured and the second time interval at which the second information is repeatedly measured.

13. The sensing method according to claim 11, further comprising:
shortening the second time interval at which the second information is repeatedly measured, when the first information does not satisfy the first criterion.

14. The sensing method according to claim 11, further comprising:
shortening the second time interval at which the second information is output according to a frequency at which the first information does not satisfy the first criterion and the second information does not satisfy the second criterion.

15. The sensing method according to claim 10, wherein the second time interval at which the second information is measured is longer than the first time interval at which the first information is measured.

16. The sensing method according to claim 10, further comprising:
shortening the at least one of the first time interval at which the first information is measured and the second time interval at which the second information is measured when the first information does not satisfy a first criterion or when the second information does not satisfy a second criterion.

17. The sensing method according to claim 10, further comprising:
change the first time interval at which the first information is measured by selectively removing measurements of the first information; and
change the second time interval at which the second information is measured by selectively removing measurements of the second information.

18. The sensing method according to claim 10, further comprising:
displaying at least one of the first information and the second information on display device based on the first time interval at which the first information is measured and the second time interval at which the second information is measured.

* * * * *